United States Patent [19]

Heidgen

[11] Patent Number: Plant 5,310

[45] Date of Patent: Oct. 30, 1984

[54] GERANIUM 'FIREWORKS'

[76] Inventor: Charles F. Heidgen, 821 Walnut St., Batavia, Ill. 60510

[21] Appl. No.: 442,654

[22] Filed: Jan. 3, 1983

[51] Int. Cl.[3] ..... A01H 5/00

[52] U.S. Cl. ..... Plt./68

[58] Field of Search ..... Plt./68

*Primary Examiner*—James R. Feyrer

[57] ABSTRACT

A new and distinct variety of geranium plant, Fireworks, characterized by its cascading growth habit; its continuous and exceptionally prolific blooming habit; its striking, almost primitive, single flower; and its distinctive dark green leaves with extremely dark zonation.

1 Drawing Figure

The present discovery, hereinafter referred to by the cultivar name, Fireworks, relates to a new and distinct geranium plant.

BACKGROUND

Fireworks is a new and improved variety which has resulted from definite breeding programs and experiments carried on by me in my greenhouses at 821 Walnut Street, Batavia, Ill. Our experiments commenced in March, 1977 and are being carried on continuously. This seedling, 78×027A (C-10), resulted from a cross between Frank Headley, an unpatented, variegated foliage dwarf geranium and Stadtbern, an unpatented standard zonal geranium.

Asexual reproduction of Fireworks has been accomplished from vegetative cuttings in my greenhouses in Batavia, Ill. Examination of plants so propagated has demonstrated that the combination of characteristics herein disclosed for Fireworks are firmly fixed and retained through successive generations of asexual reproduction.

SUMMARY

The new and patentable characteristics of Fireworks reside in its cascading growth habit, its continuous and exceptionally prolific blooming habit, its distinctive medium-sized dark green leaves with extremely dark zonation and its striking, almost primitive, single flower.

DESCRIPTION OF DRAWING

The photograph shows the plant and flower of a fully developed geranium of the new variety, Fireworks.

BOTANIC DESCRIPTION

The plant

Growth: Fireworks is an exceptionally prolific bloomer. The florets are single, almost primitive (ray type), with the two upper petals being slightly narrower and shorter than the lower three petals. The flower head (truss) is of medium size and moderately resistant to shattering. The growth is procumbent in habit giving a cascading effect. Growth rate is rapid, producing a typical 10" flowering basket in 10–12 weeks from four 2¼" plants using standard commercial culture.

Blooming habit: Exceptionally prolific and continuous bloomer, throughout the year, outdoors or in the greenhouse. A mature 10" basket commonly produces 20–24 heads at one time.

Inflorescence: Medium-size, open head, somewhat rounded, measuring 3½–4 inches in diameter.

Foliage:

*Quantity.*—Abundant.

*Size.*—Small, 1–2½ inches across.

*Color.*—Ivy Green (0001060/2) with Oxblood Red (00823) zone. (The Royal Horticultural Society Horticultural Colour Chart).

*Texture.*—Slightly pubescent upper surface and lower surface.

Stem: Slim, short internodes, free branching, procumbent habit, rapid grower.

Petiole: Short, slightly longer than leaf. Same color as leaf.

The flower

Truss:

*Size.*—Medium-size, 3½–4 inches in diameter.

*Shape.*—Open, a flattened globe as it opens.

*Number of florets.*—Variable, range from 4–15, average 10–11.

*Lasting quality.*—Average. Blooms remain 5–12 days, longer if cool and dry.

Bud:

*Sepals.*—Short, slightly pointed.

*Color.*—Cherry Red (722/1) (The Royal Horticultural Society Horticultural Colour Chart).

*Form.*—Pointed.

Florets:

*Size.*—1¼–1½ Inches.

*Petalage.*—Single, five.

*Color.*—Dutch Vermillion (717) (The Royal Horticultural Society Horticultural Colour Chart). Color fades with age.

Texture: Soft and glowing.

Form: Modified primitive, upper petals ¼" wide, lower petals ⅜" wide.

Lasting quality: Average floret lasts 4–8 days. The truss lasts up to 10–12 days.

Behavior: Once the plant starts to bloom its exceptionally prolific blooming habit yields a striking display of soft glowing scarlet against the small dark-zoned foliage.

Having thus disclosed my invention, I claim:

1. A new and distinct variety of geranium plant, substantially as shown and described, characterized by its cascading growth habit; its continuous and exceptionally prolific blooming habit; its striking, almost primitive, single flower; and its distinctive dark green leaves with extremely dark zonation.

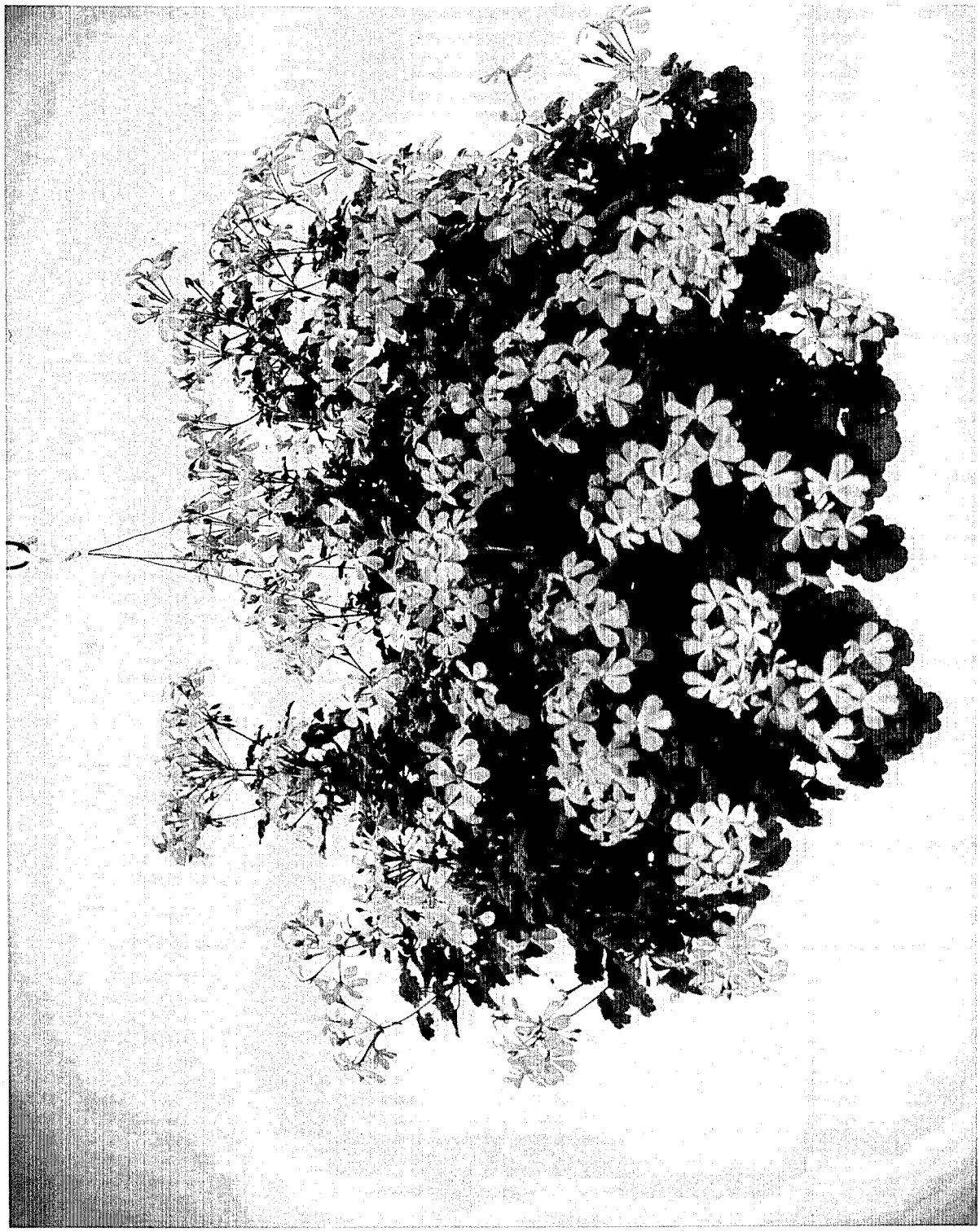

* * * * *